US00PP14695P29

(12) United States Plant Patent
Bradford

(10) Patent No.: US PP14,695 P2
(45) Date of Patent: Apr. 13, 2004

(54) PEACH TREE NAMED 'BRIGHT PRINCESS'

(50) Latin Name: *Prunus persica*
Varietal Denomination: Bright Princess

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 151 days.

(21) Appl. No.: 10/300,613

(22) Filed: Nov. 21, 2002

(51) Int. Cl.[7] ..... A01H 5/00

(52) U.S. Cl. ..... Plt./198

(58) Field of Search ..... Plt./198

(56) References Cited

U.S. PATENT DOCUMENTS

PP7,066 P 12/1989 Bradford
PP7,507 P 4/1991 Bradford

*Primary Examiner*—Anne Marie Grunberg

(57) ABSTRACT

The present invention relates to a peach tree, *Prunus persica*, and more particularly to a new and distinct variety characterized by a medium size, vigorous, hardy, self-fertile, productive and regular bearing tree. The fruit matures under the ecological conditions described in the latter part of June, with first picking on Jun. 22, 2002. The fruit is uniformly large in size, sweet and acidic in flavor, globose in shape, freestone in type, firm in texture, yellow in flesh color, and mostly red in skin color. The variety was developed as a first generation cross using 'Spring Bright' (U.S. Plant Pat. No. 7,507) yellow flesh nectarine as the selected seed parent and an unnamed peach as the selected pollen parent.

1 Drawing Sheet

Cross reference to related applications: This case is related to co-pending U.S. Plant Patent Application filed concurrently as Peach Tree Named 'Spring Candy'.

Botanical classification: *Prunus persica.*

Variety denomination: 'Bright Princess'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'Bright Princess'. The present variety was hybridized by me in 1996, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using 'Spring Bright' (U.S. Plant Pat. No. 7,507) yellow flesh nectarine as the selected seed parent and an unnamed peach as the selected pollen parent. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Spring Bright' (U.S. Plant Pat. No. 7,507) nectarine, by producing fruit that is globose in shape, firm and crisp in texture, mostly red in skin color, yellow in flesh color, and that ripen in the latter part of June, but is very distinguished therefrom by producing fruit that is freestone instead of clingstone and that is peach instead of nectarine in type.

The present variety is similar to the cross referenced 'Spring Candy' peach by sharing the same parentage and by producing peaches that are freestone in type, nearly full red in skin color, yellow in flesh color, and firm in texture, but differs significantly by producing peaches that have the classical acidic peach flavor instead of sub-acidic, that have considerably less red streaking around the stone, that mature about 3 days earlier, and that have a sweet kernel instead of bitter.

The present variety is most similar to 'Diamond Princess' (U.S. Plant Pat. No. 7,066) peach by producing fruit that is yellow in flesh color, nearly full red in skin color, excellent in flavor, and freestone in type, but is distinguished therefrom by blooming about one week earlier and by producing fruit that is firmer in texture, larger in size, and matures about fifteen days earlier.

SUMMARY OF VARIETY

In summary, the present variety is characterized by a medium size, vigorous, hardy, self-fertile, productive and regular bearing tree. The fruit matures under the ecological conditions described in the latter part of June, with first picking on Jun. 22, 2002. The fruit is uniformly large in size, sweet and acidic in flavor, globose in shape, freestone in type, firm in texture, yellow in flesh color, and mostly red in skin color.

DRAWING

The accompanying photograph exhibits four whole fruits positioned to display the characteristics of the skin color and form, one fruit divided along the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 27, 2002, on the original tree during its sixth growing season. All major color code designations are by reference to the Inter-Society Color Council, National Bureau of Standards. Common color names are also used occasionally.

TREE

Size: Medium, reaching a height of 9' [2.74 m.] and a spread of 9' [2.74 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 3" [76 mm.] after the sixth growing season.

*Texture.*—Shaggy.

*Bark color.*—Brownish gray [64. brGy] with Grayish reddish Brown [46. gy.rBr] streaking.

*Lenticels.*—Approximate number per square inch: 14. Color: Light yellowish brown [76. l.yBr]. Average Size: ⅜" [9.5 mm.].

Branches:

*Size.*—Diameter of limb is 1" [25 mm.] measured 12" above the secondary fork, typical of *Prunus persica*, and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Moderate brown [58. m.Br].

*Lenticels.*—Approximate number per square inch: 30. Color: Light orange yellow [70. l.OY]. Typical size: 1/16" to ¼" [1.6–6.4 mm.].

Leaves:

*Size.*—Medium. Average Length: 5½" [140 mm.]. Average width: 1⅝" [41 mm.].

*Arrangemet.*—Alternate.

*Thickness.*—Medium.

*Form.*—Elliptical.

*Apex.*—Acuminate.

*Base.*—Rounded.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Number: 2 per leaf, up to 6 per growing tip. Average Length: 5/16" [7.9 mm.]. Color: Light yellow green [119. l. YG] when growing.

*Glands.*—Number: 2 to 4. Position: Usually one pair alternately or oppositely positioned on the petiole with the remainder on the base of leaf blade. Size: Medium. Form: Reniform. Color: Light yellow green [119. 1.YG] on younger leaves acquiring Dark reddish brown [44. d.rBr] centers with age.

*Leaf buds.*—Conic.

Flower buds:

*Hardiness.*—Hardy, with respect to central California winters.

*Diameter.*—Typically ⅜" [9.5 mm.] 1 week before bloom.

*Length.*—Typically ¾" [19.1 mm.] 1 week before bloom.

*Form.*—Not appressed.

*Surface.*—Pubescent.

*Color.*—Moderate purplish red [258.m.pR].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Most often five, with up to forty percent double blossoms observed.

*Petal shape.*—Circular to elliptical.

*Petal margin.*—Very wavy.

*Average petal diameter.*—15/16" [23.8 mm.].

*Average petal length.*—¾" [19.1 mm.].

*Petal apex.*—Rounded.

*Petal base.*—Rounded to somewhat acute.

*Petal color.*—Light purplish pink [249. l.pPk].

*Anther color.*—Dark red [16. d.R] over Light orange yellow [70. l.OY] centers.

*Stigma color.*—Light greenish yellow [101. l.gY].

*Sepal color.*—Grayish purplish red [262. gy.pR].

*Sepal length.*—9/32" [7 mm.].

*Sepal width.*—3/16" [5 mm.].

*Average pistil length.*—¾" [19.1 mm.].

*Average stamen length.*—⅝" [15.9 mm.].

*Fragrance.*—Moderate when nectar is present.

*Blooming period.*—Early to medium compared with other varieties.

*Onset of bloom.*—One percent on Feb. 28, 2002.

*Date of full bloom.*—Mar. 8, 2002.

*Duration of bloom.*—One to two weeks, dependent on ambient temperature.

*Number per cluster.*—1 to 3, with single flowers most common.

FRUIT

Maturity when described: Firm ripe, Jun. 27, 2002.

Date of first picking: Jun. 22, 2002.

Date of last picking: Jul. 2, 2002.

Size: Uniform, large.

*Average diameter axially.*—2 13/16" [71.4 mm.].

*Average diameter across suture plane.*—2 15/16" [74.6 mm.].

*Typical weight.*—7.4 ounces [210 grams].

Form: Uniform, symmetrical, primarily globose with slight axial compression.

*Longitudinal section form.*—Circular to slightly elliptical.

*Transverse selection through diameter.*—Circular.

Suture: A distinct line toward the base and along the side becoming a shallow groove near the apex and ending with a slight depression just beyond the pistil point, with occasional stitching typical.
Ventral surface: Rounded, with only slight lipping on one side toward the apex.
Lips: Slightly unequal.
Cavity: Flaring, elongated in the suture plane, suture showing on one side, with Brilliant yellow [83. brill.Y] stem markings typical.
*Depth.*—5/8" [15.9 mm.].
*Breadth.*—3/4" [19.1 mm.].
Base: Somewhat truncate.
Apex: Rounded.
Pistil point: Both apical and oblique, negligible in length, depressed within the suture.
Stem: Medium.
*Average length.*—7/16" [11.1 mm.].
*Average width.*—3/16" [4.8 mm.].
Skin:
*Thickness.*—Medium.
*Texture.*—Pubescent.
*Tenacity.*—Tenacious to flesh.
*Astringency.*—Nonastringent.
*Tendency to crack.*—None observed.
*Color.*—Very deep red [14. v.deep R] over a Moderate red orange [37. r.O] background, with slight streaking typical.
Down: Moderately abundant, medium in length, rolls up when rubbed.
Flesh:
*Color.*—Brilliant yellow [83. brill.Y] with a minimal amount of Moderate red [15. m.R] streaking very close to the stone.
*Surface of pit cavity.*—Dark yellowish pink [30. d.yPk] fibers.
*Amygdalin.*—Moderate.
*Juice.*—Abundant, rich.
*Texture.*—Firm and crisp.
*Fibers.*—Abundant, fine.
*Ripens.*—Slightly earlier toward the apex and along the suture.
*Flavor.*—Excellent balance of acid and sugar, 14 to 15 brix.
*Aroma.*—Moderate.
*Eating quality.*—Excellent.

STONE

Type: Freestone.
Form: Oval.
Hilum: Narrow.
Base: Slightly oblique.
Apex: Acute, with an average tip length of 3/32" [2.4 mm.].
Sides: Equal.
Surface: Irregularly furrowed near the apex and pitted toward the base.
Ridges: Jagged toward the base.
External color: Strong reddish brown [40. s.rBr] when freshly removed.
Internal color when cracked: Moderate yellowish brown [77. m.yBr].
Average pit wall thickness: 1/4" [6.4 mm.].
Average width: 7/8" [22.2 mm.].
Average length: 1½" [38.1 mm.].
Average breadth: 11/16" [17.5 mm.].
Tendency to split: None observed.
Kernel:
*Form.*—Oval.
*Pellicle color.*—Grayish yellow [90. gy.Y].
*Skin color.*—Light yellow [86. l.Y] when freshly removed.
*Vein color.*—Moderate orange yellow [71. m.OY].
*Taste.*—Sweet.
*Viable.*—Yes.
*Average width.*—7/16" [11.1 mm.].
*Average length.*—11/16" [17.5 mm.].
*Amygdalin.*—Scant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Diamond Princess' (U.S. Plant Pat. No. 7,066) peach by producing fruit that is yellow in flesh color, nearly full red in skin color, excellent in flavor, and freestone in type, but is distinguished therefrom by blooming about one week earlier and by producing fruit that is firmer in texture, larger in size, and matures about fifteen days earlier.

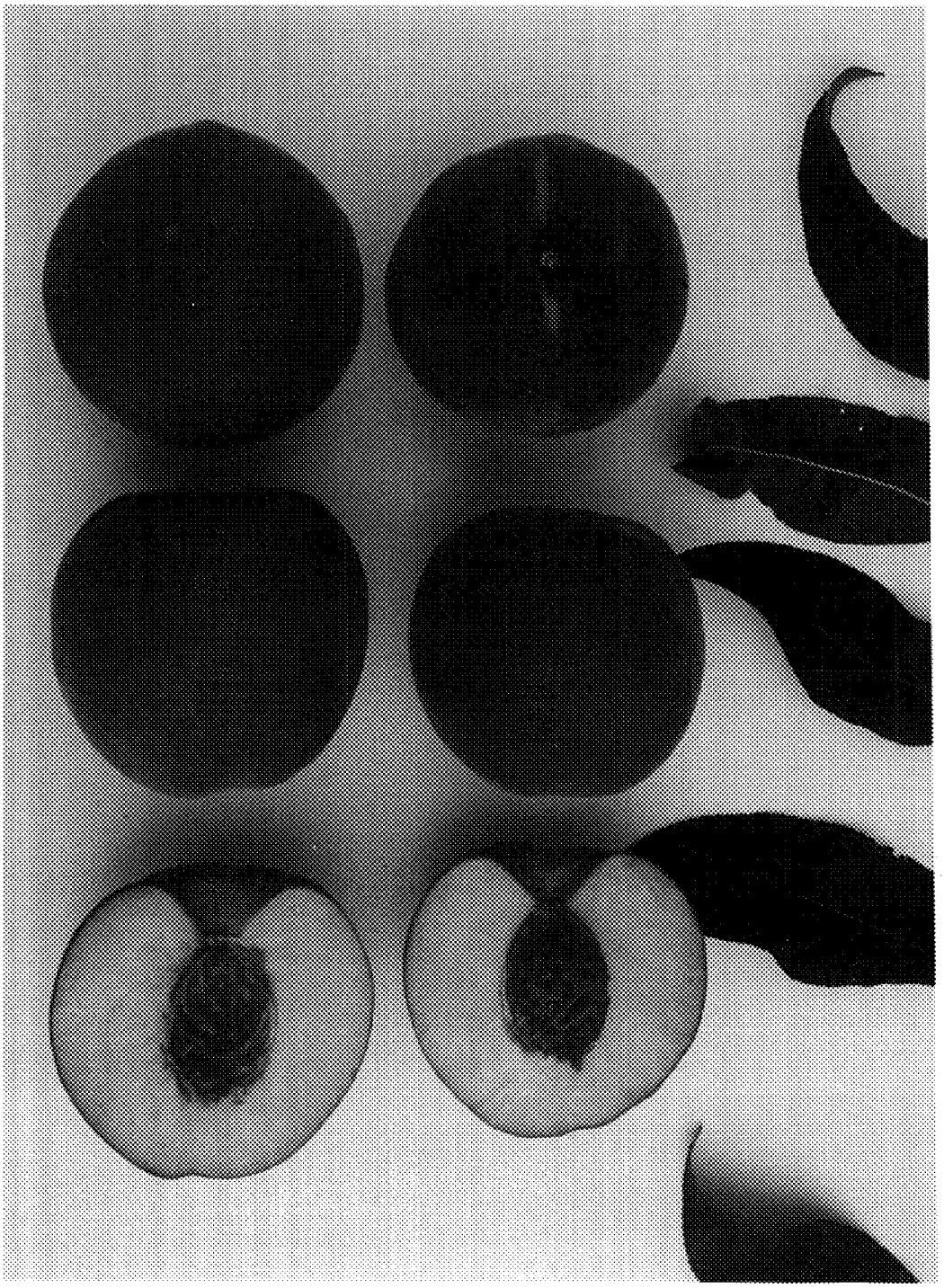

* * * * *